(12) United States Patent
Klute et al.

(10) Patent No.: US 11,026,814 B2
(45) Date of Patent: Jun. 8, 2021

(54) PIVOT-FLEX FOOT

(71) Applicant: UNIVERSITY OF WASHINGTON, Seattle, WA (US)

(72) Inventors: Glenn Klute, Seattle, WA (US); Nathan Michael Olson, Seattle, WA (US)

(73) Assignee: University of Washington, Seattle, WA (US)

(*) Notice: Subject to any disclaimer, the term of this patent is extended or adjusted under 35 U.S.C. 154(b) by 247 days.

(21) Appl. No.: 16/308,044

(22) PCT Filed: Jun. 8, 2017

(86) PCT No.: PCT/US2017/036480
§ 371 (c)(1),
(2) Date: Dec. 7, 2018

(87) PCT Pub. No.: WO2017/214351
PCT Pub. Date: Dec. 14, 2017

(65) Prior Publication Data
US 2019/0307581 A1 Oct. 10, 2019

Related U.S. Application Data

(60) Provisional application No. 62/347,415, filed on Jun. 8, 2016.

(51) Int. Cl.
*A61F 2/66* (2006.01)
*A61F 2/60* (2006.01)
(Continued)

(52) U.S. Cl.
CPC .................. *A61F 2/66* (2013.01); *A61F 2/60* (2013.01); *A61F 2/6607* (2013.01); *A61F 2/76* (2013.01);
(Continued)

(58) Field of Classification Search
CPC ...... A61F 2/50; A61F 2/60; A61F 2/66; A61F 2/76; A61F 2002/6614; A61F 2002/6628;
(Continued)

(56) References Cited

U.S. PATENT DOCUMENTS 4,892,554 A    1/1990  Robinson
5,116,384 A *  5/1992  Wilson ...................... A61F 2/66
                                                    623/49

(Continued)

FOREIGN PATENT DOCUMENTS

WO    WO 2012/009319    1/2012

OTHER PUBLICATIONS

Miller et al., "The prevalence and risk factors of falling and fear of falling among lower extremity amputees," Arch Phys Med Rehabil 82(8): p. 1031-7 (2001).
(Continued)

*Primary Examiner* — Christie L Bahena
(74) *Attorney, Agent, or Firm* — McDonnell Boehnen Hulbert & Berghoff LLP (57) ABSTRACT

A prosthetic device is provided including (a) an ankle component, (b) a foot component coupled to the ankle component, wherein the foot component has a longitudinal length extending at least partially along a sagittal plane of a user when the prosthetic device is in use, wherein the foot component has a thickness extending at least partially along a transverse plane of a user when the prosthetic device is in use, and (c) a coupling mechanism positioned between the foot component and the ankle component, wherein the coupling mechanism couples a rotation of the foot component with respect to the sagittal plane to a rotation of the foot component with respect to the transverse plane.

20 Claims, 7 Drawing Sheets

(51) Int. Cl.
A61F 2/76 (2006.01)
A61F 2/50 (2006.01)
(52) U.S. Cl.
CPC ............. A61F 2002/5001 (2013.01); A61F
2002/5007 (2013.01); A61F 2002/665
(2013.01); A61F 2002/6621 (2013.01); A61F
2002/6642 (2013.01); A61F 2002/6664
(2013.01); A61F 2002/6671 (2013.01)
(58) Field of Classification Search
CPC ...... A61F 2002/6607; A61F 2002/5007; A61F
2002/6621; A61F 2002/6642; A61F
2002/665; A61F 2002/6664; A61F
2002/6671
See application file for complete search history.

(56) References Cited

U.S. PATENT DOCUMENTS

| | | | |
|---|---|---|---|
| 6,443,995 | B1 | 9/2002 | Townsend et al. |
| 7,374,578 | B2 | 5/2008 | Townsend et al. |
| 7,618,464 | B2 | 11/2009 | Christensen |
| 8,685,109 | B2 | 4/2014 | Clausen et al. |
| 2005/0267603 | A1 | 12/2005 | Lemonte et al. |
| 2007/0100466 | A1 | 5/2007 | Allert |
| 2007/0106396 | A1 | 5/2007 | Doodroe et al. |
| 2012/0078380 | A1 | 3/2012 | Jonsson et al. |
| 2013/0144403 | A1* | 6/2013 | Lecomte ............ A61F 2/66 623/33 |
| 2014/0039642 | A1* | 2/2014 | Nijiman ............. A61F 2/66 623/33 |
| 2016/0151175 | A1 | 6/2016 | Klute et al. |

OTHER PUBLICATIONS

Montori et al., "Progress in evidence-based medicine," JAMA, 300(15): p. 1814-6 (2008).
Morse, "Determining Sample Size," Qual Health Res, 10(1): p. 3-5 (2000).
National Researh Council, "Terminal research reports on artificial limbs," Neely Printing Company, Inc., 100 pages (1947).
Naylor, "Experimental friction blisters," British Journal of Dermatology, 67(10):327-342, (1955).
Nehler et al., "Functional outcome in a contemporary series of major lower extremity amputations," Journal of vascular surgery, 38(1): p. 7-14 (2003).
Nielsen, "A Survey of Amputees: Functional Level and Life Satisfaction, Information Needs, and the Prosthetist's Role," Journal of Prosthetics and Orthotics vol. 3, No. 3 125-129 (1991).
Nolan et al., "Adjustments in gait symmetry with walking speed in trans-femoral and trans-tibial amputees," Gait & posture, 17(2):142-151, (2003).
Nolan et al., "The functional demands on the intact limb during walking for active trans-femoral and trans-tibial amputees," Prosthetics and orthotics international, 24(2):117-125, (2000).
Norvell et al., "Defining successful mobility after lower extremity amputation for complications of peripheral vascular disease and diabetes," Journal of Vascular Surgery 54(2): p. 412-9 (2011).
Norvell et al., "The development and validation of a novel outcome measure to quantify mobility in the dysvascular ower extremity amputee: the amputee single item mobility measure," Clin Rehabil. Sep.; 30(9): 878-889 (2016).
O'Connor, "Validation of a decisional conflict scale," Medical decision making, 15(1): p. 25-30 (1995).
Olson et al., "Design of a transtibial prosthesis with active transverse plane control," Journal of Medical Devices, 9 (4): p. 045002 (2015).
Orendurff et al., "The kinematics and kinetics of turning: limb asymmetries associated with walking a circular path," Gait Posture 23(1): p. 106-11 (2006).

Pai et al., "The compressive mechanical properties of diabetic and non-diabetic plantar soft tissue," J Biomech, 43(9): p. 1754-60 (2010).
Patzkowski et al., "The changing face of disability in the US Army: the Operation Enduring Freedom and Operation Iraqi Freedom effect," J Am Acad Orthop Surg, 20 Suppl 1: p. S23-30 (2012).
Pedlow et al., "Patient perspectives on information needs for amputation secondary to vascular surgery: What, when, why, and how much?," Journal of Vascular Nursing, 32(3): p. 88-98 (2014).
Pernot et al., "Daily functioning of the lower extremity amputee: an overview of the literature," Clin Rehabil 11(2): 93-106 (1997).
Petre et al., "Optimization of nonlinear hyperelastic coefficients for foot tissues using a magnetic resonance imaging deformation experiment," Journal of Biomechanical Engineering, 135(6): p. 61001-12. (2013).
Pew et al., "Design of Lower Limb Prosthesis Transverse Plane Adaptor with Variale Stiffness," Journal of Medical Device vol. 9, Issue 3, Article 035001 (2015).
Pew, "Design and testing of a variable stiffness transverse plane adaptor for use in a lower limb prosthesis," Master's thesis, University of Washington, (2014).
Pezzin et al., "Use and Satisfaction with Prosthetic Limb Devices and Related Services," Archives of Physical Medicine and Rehabilitation 85(5):723-9 (2004).
Pratt et al., "Series elastic actuators," In Intelligent Robots and Systems 95.'Human Robot Interaction and Cooperative Robots', Proceedings. 1995 IEEE/RSJ International Conference on, vol. 1, pp. 399-406. IEEE, (1995).
Pratt et al., The roboknee: an exoskeleton for enhancing strength and endurance during walking in Robotics and Automation, 2004. Proceedings. ICRA'04. 2004 IEEE International Conference on, vol. 3, pp. 2430-2435. IEEE, (2004).
Rabiner et al., "An introduction to hidden Markov models," IEEE ASSP Magazine, 3: p. 4-16 (1986).
Racette et al., "Clinical experience and functional considerations of axial rotators for the amputee." Orthotics and prosthetics, 31(2): 29-33, (1977).
Rao et al., "Musculoskeletal conditions of the foot and ankle: assessments and treatment options," Best Pract Res Clin Rheumatol, 26(3): p. 345-68 (2012).
Rao et al., "Segment velocities in normal and transtibial amputees: prosthetic design implications," Rehabilitation Engineering, IEEE Transactions on, 6(2):219-226, (1998).
Resnik et al., "Reliability of outcome measures for people with lower-limb amputations: distinguishing true change from statistical error," Phys Ther 91(4): 555-65 (2011).
Robinson et al., "Series elastic actuator development for a biomimetic walking robot," In Advanced Intelligent Mechatronics, 1999. Proceedings. 1999 IEEE/ASME International Conference on, pp. 561-568. IEEE, (1999).
Roffman et al., "Predictors of non-use of prostheses by people with lower limb amputation after discharge from rehabilitation: development and validation of clinical prediction rules," J Physiother 60(4): 224-31 (2014).
Rommers et al., "Mobility of people with lower limb amputations: scales and questionnaires: a review," Clin Rehabil 15(1): 92-102 (2001).
Rouse et al., "The difference between stiffness and quasi-stiffness in the context of biomechanical modeling," Biomedical Engineering, IEEE Transactions on, 60(2):562-568,( 2013).
Ryall et al., "Is the Rivermead Mobility Index appropriate to measure mobility in lower limb amputees?," Disabil Rehabil 25(3): 143-53 (2003).
Ryall et al., "The SIGAM mobility grades: a new population-specific measure for lower limb amputees," Disabil Rehabil 25(15): 833-44 (2003).
Sadeghi et al., "Muscle power compensatory mechanisms in below-knee amputee gait," American journal of physical medicine & rehabilitation, 80(1):25-32, (2001).
Saltzman et al., "Epidemiology of ankle arthritis: report of a consecutive series of 639 patients from a tertiary orthopaedic center Iowa," Orthop J, 25: p. 44-6 (2005).

(56) References Cited

OTHER PUBLICATIONS

Sandelowski, "Sample size in qualitative research," Res Nurs Health, 18(2): p. 179-83 (1995).
Sansam et al., "Predicting walking ability following lower limb amputation: a systematic review of the literature," J Rehabil Med 41(8): 593-603 (2009).
Schmid et al., "Conservative treatment of asymmetric ankle osteoarthritis," Foot and ankle clinics, 18(3): p. 437-48 (2013).
Schoppen et al., "Physical, mental, and social predictors of functional outcome in unilateral lower-limb amputees," Arch Phys Med Rehabil 84(6): 803-11 (2003).
Segal et al., "Comparison of transtibial amputee and non-amputee biomechanics during a common turning task," Gait & Posture Jan.;33(1):41-7 (2011).
Segal et al., "Does a torsion adapter improve functional mobility, pain, and fatigue in patients with transtibial amputation?," Clinical Orthopaedics and Related Research, 472(10): p. 3085-92 (2014).
Segal et al., "Local dynamic stability in turning and straight-line gait," Journal of biomechanics, 41(7):1486-1493, (2008).
Segal et al., "Local dynamic stability of amputees wearing a torsion adapter compared to a rigid adapter during straight-line and turning gait," J Biomech, 43(14): p. 2798-803 (2010).
Segal et al., "Transtibial amputee joint rotation moments during straight-line walking and a common turning task with and without a torsion adapter," J Rehabil Res Dev, 46(3): p. 375-83 (2009).
Belles et al., "Effects of prosthetic mass and mass distribution on kinematics and energetics of prosthetic gait: a systematic review," Archives of physical medicine and rehabilitation, 80(12):1593-1599, (1999).
Bepucha et al., "Establishing the effectiveness of patient decision aids: key constructs and measurement instruments," BMC medical informatics and decision making, 3(Suppl 2): p. S12 (2013).
Seroussi et al., "Mechanical work adaptations of above-knee amputee ambulation," Archives of physical medicine and rehabilitation, 77(11):1209-1214, (1996).
Bhibuya et al., "Prevalence of podiatric medical problems in veterans versus nonveterans," J Am Podiatr Med Assoc, 101(4): p. 323-30 (2011).
Huang et al., "A strategy for identifying locomotion modes using surface electromyography," IEEE transactions on bio-medical engineering, 56: p. 65-73 (2009).
Huang et al., "Continuous locomotion-mode identification for prosthetic legs based onneuromuscular-mechanical fusion," IEEE transactions on bio-medical engineering 58: p. 2867-7 (2011).
Huang et al., "Effects of ankle-foot orthoses on ankle and foot kinematics in patient with ankle osteoarthriti," Arch Phys Med Rehabil, 87(5): p. 710-6 (2006).
Huch et al., "Osteoarthritis in ankle and knee joints." Semin Arthritis Rheum 26(4): p. 667-74 (1997).
Hurd et al., "Differences in normal and perturbed walking kinematics between male and female athletes," Clinical Biomechanics, 19(5):465-472, (2004).
Hutter et al., "High compliant series elastic actuation for the robotic leg scarleth," In Proc. of the International Conference on Climbing and Walking Robots (CLAWAR), No. EPFL-CONF175826, (2011).
Isvilanonda et al., "Finite element analysis of the foot: Model validation and comparison between two common treatments of the clawed hallux deformity," Clinical Biomechanics, 27(8): p. 837-44 (2012).
Isvilanonda et al., "Hyperelastic compressive mechanical properties of the subcalcaneal soft tissue: An inverse finite element analysis," Journal of Biomechanics, 49(7): p. 1186-1191 (2016).
Isvilanonda, "Finite Element Modeling of the Foot, in Mechanical Engineering," University of Washington. p. 207 (2015).
Jarl et al., "Validity evidence for a modified version of the Orthotics and Prosthetics Users' Survey," Disabil Rehabil Assist Technol. [Journal article] 7(6): 469-478 (2012).
Johnson et al., "Pre and post-amputation mobility of trans-tibial amputees: correlation to medical problems, age and mortality," Prosthet Orthot Int 19(3): 159-64 (1995).
Judge et al., "Effects of age on the biomechanics and physiology of gait,"Clin Geriatr Med, 12(4): p. 659-78 (1996).
Judge et al., "Step length reductions in advanced age: the role of ankle and hip kinetics," J Gerontol Med Sci, 51(6): p. M303-12 (1996).
Kadaba et al., "Measurement of lower extremity kinematics during level walking," Journal of orthopaedic research, 8 (3):383-392, (1990).
Kerrigan et al., "Gender differences in joint biomechanics during walking: normative study in young adults," American journal of physical medicine & rehabilitation, 77(1):2-7, (1998).
Kirtley et al., "Influence of walking speed on gait parameters," Journal of biomedical engineering, 7(4):282-288, (1985).
Klute et al., "Does activity effect residual limb skin temperatures? Clinical Orthopaedics & Related Research," 427 (10): p. 3062-3067 (2014).
Klute et al., "Prosthesis management of residual-limb perspiration with subatmospheric vacuum pressure," Journal of Rehabilitation Research and Development 53(6): p. 721-728 (2016).
Klute et al., "Prosthetic intervention effects on activity of lower-extremity amputees," Arch Phys Med Rehabil, 87(5): p. 717-22 (2006).
Kohler et al., "Feasibility of using a checklist based on the International Classification of Functioning, Disability and Health as an outcome measure in individuals following lower limb amputation," Prosthet Orthot Int 35(3): 294-301 (2011).
Koncicki et al., "Communication Skills and Decision Making for Elderly Patients With Advanced Kidney Disease: A Guide for Nephrologists,"American Journal of Kidney Diseases 67(4): p. 688-695 (2016).
Krausz et al., "Depth Sensing for Improved Control of Lower Limb Prostheses," IEEE transactions on biomedical engineering 62(11): 2576-87 (2015).
Kulkarni et al., "Chronic low back pain in traumatic lower limb amputees," Clinical Rehabilitation, 19(1):81-86, (2005).
Lamoureux et aL, "Functional Analysis of the UC-BL Shank Axial Rotation Device," Prosthetics and Orthotics International vol. 1, Issue 2, 114-118 (1977).
Landry et al., "Predictors of healing and functional outcome following transmetatarsal amputations," Archives of Surgery, 146(9): p. 1005-1009 (2011).
Lawrence et aL, "Estimates of the prevalence of arthritis and other rheumatic conditions in the United States. Part II," Arthritis Rheum 58(1): p. 26-35 (2008).
Legro et al., "Issues of importance reported by persons with lower limb amputations and prostheses," Journal of Rehabilitation Research and Development Jul.;36(3):155-63 (1999).
Lehmann et al., "Mass and mass distribution of below-knee prostheses: effect on gait efficacy and self-selected walking speed," Archives of Physical Medicine and Rehabilitation, 79(2): p. 162-8 (1998).
Lelas et al., "Predicting peak kinematic and kinetic parameters from gait speed," Gait & posture, 17(2):106-112, (2003).
Lemarie et al., "Osteoarthritis and elderly amputee gait," Archives of physical medicine and rehabilitation, 75:1094-1099, (1994).
Lerman et al., "Patients' perceived involvement in care scale," Journal of General Internal Medicine, 5(1): p. 29-33 (1990).
Levens et al., "Transverse rotation of the segments of the lower extremity in locomotion," The Journal of Bone & Joint Surgery, 30(4):859-872, (1948).
Levy, "Amputees: skin problems and prostheses," Cutis 55(5): p. 297-301 (1995).
Levy, "Skin problems of the leg amputee," Prosthetics and Orthotics International Apr.;4(1):37-44 (1980).
Li et al., Declining rates of hospitalization for nontraumatic lower-extremity amputation in the diabetic population aged 40 years or older: U.S.,1988-2008, Diabetes Care 35(2): p. 273-7 (2012).
Lin-Chan et al., "The effects of added prosthetic mass on physiologic responses and stride frequency during multiple speeds of walking in persons with transtibial amputation," Archives of Physical Medicine and Rehabilitation, 84(12): p. 1865-71 9 (2003).
Lundberg et al., "The axis of rotation of the ankle joint," Journal of Bone & Joint Surgery, British Volume, 71(1):94-99, (1989).

(56) References Cited

OTHER PUBLICATIONS

Lundberg et al., Kinematics of the ankle /foot complex-Part 3: Influence of leg rotation. Foot and Ankle 9(6): p. 304-309 (1989).
Lundgren et al., "Invasive in vivo measurement of rear-, mid- and forefoot motion during walking," Gait Posture, 28 (1): p. 93-100 (2008).
Mayfield et al., "Survival following lower-limb amputation in a veteran population," J Rehabil Res Dev, 38(3): p. 341-5 (2001).
Mayfield et al., "Trends in lower limb amputation in the Veterans Health Administration, 1989-1998," J Rehabil Res Dev, 37(1): p. 23-30 (2000).
McCaffery, "The challenge of shared decision making among patients with lower literacy: a framework for research and development," Medical Decision Making Jan.-Feb.;30(1):35-44 (2009).
McCallum et al., "Transmetatarsal amputation: a case series and review of the literature," Journal of aging research, 2012. (2012).
McGibbon, "Toward a better understanding of gait changes with age and disablement: neuromuscular adaptation," Exerc Sport Sci Rev, 31(2): p. 102-8 (2003).
McHorney et al, "Individual-patient monitoring in clinical practice: are available health status surveys adequate?," Qual Life Res 4(4): 293-307 (1995).
Melzer et al., "Comparative study of osteoarthritis of the contralateral knee joint of male amputees who do and do not play volleyball," The Journal of rheumatology, 28(1):169-172, (2001).
Meulenbel et al., "Skin problems in lower limb amputees: an overview by case reports," Journal of the European Academy of Dermatology and Venereology Feb.;21(2):147-55 (2007).
Miller et al., "Myoelectric Walking Mode Classification for Transtibial Amputees," IEEE Trans Biomed Engr, 60(10): p. 2745-2750 (2003).
Miller et al., "Lower extremity prosthetic mobility: a comparison of 3 self-report scales," Arch Phys Med Rehabil 82 (10): 1432-40 (2001).
Miller et al., "The influence of falling, fear of falling, and balance confidence on prosthetic mobility and social activity among individuals with a lower balance confidence on prosthetic mobility and social activity among individuals with a lower extremity amputation," Arch Phys Med Rehabil 82(9): 1238-44 (2001).
Silverman et al., "Compensatory mechanisms in below-knee amputee gait in response to increasing steady-state walking speeds," Gait & posture, 28(4):602-609, (2008).
Silverman et al., "Differences in whole-body angular momentum between below-knee amputees and non-amputees across walking speeds," Journal of biomechanics, 44(3):379-385, (2011).
Sinitski et al., "Biomechanics of the ankle-foot system during stair ambulation: Implications for design of advanced ankle-foot prostheses," Journal of biomechanics, 45(3):588-594, (2012).
Smith et al., "Gender differences in pelvic motions and center of mass displacement during walking: stereotypes quantified," Journal of women's health & gender-based medicine, 11(5):453-458, (2002).
Smith et al., "Oscillation and reaction board techniques for estimating inertial properties of a below-knee prosthesis," Journal of visualized experiments: JoVE, (87), (2014).
Smith et al., "Phantom limb, residual limb, and back pain after lower extremity amputations," Clinical orthopaedics and related research, 361:29-38, (1999).
Solari et al., "Role preferences of people with multiple sclerosis: image-revised, computerized self-administered version of the control preference scale," PLoS One, 8(6): e66127 (2013).
Spence et al., "Prevention of blisters, callosities and ulcers by absorption of shear forces," Journal of the American Podiatry Association, 58(10):428, (1968).
Spirka et al., "Simple finite element models for use in the design of therapeutic footwear," J Biomech, 47(12): p. 2948-55 (2014).
Spitzer et al., "A brief measure for assessing generalized anxiety disorder: the GAD-7," Archives of internal medicine, 166(10): p. 1092-1097 (2006).
Streppel et al., "Functional status and prosthesis use in amputees, measured with the Prosthetic Profile of the Amputee (PPA) and the short version of the Sickness Impact Profile (SIP68)," Int J Rehabil Res 24(3): 251-6 (2001).
Su et al., "Differences in gait characteristics between persons with bilateral transtibial amputations, due to peripheral vascular disease and trauma, and able-bodied ambulators," Archives of physical medicine and rehabilitation, 89 (7):1386-1394, (2008).
Su et al., "The effects of increased prosthetic ankle motions on the gait of persons with bilateral transtibial amputations," Am J Phys Med Rehabil, 89(1): p. 34-47 (2010).
Suckow et al., "Domains that Determine Quality of Life in Vascular Amputees," Annals of vascular surgery 29(4): p. 722-730. (2015).
Sup et al., "Design and control of a powered transfemoral prosthesis," The International journal of robotics research, 27(2):263-273, (2008).
Tamhane et al., "Shared decision-making in diabetes care," Current diabetes reports,15: p. 1-10 (2015).
Tashman et al., "Abnormal rotational knee motion during running after anterior cruciate ligament reconstruction," Am J Sports Med, 32(4): p. 975-83 ( 2004).
Terwee et al., "Quality criteria were proposed for measurement properties of health status questionnaires," J Clin Epidemiol 60(1): 34-42 (2007).
Tkach et al., "Neuromechanical sensor fusion yields highest accuracies in predicting ambulation mode transitions for trans-tibial amputees," IEEE Engineering in Medicine and Biology Society. Annual Conference 2013: p. 3074-7 (2013.).
Torburn et al., "Below-knee amputee gait with dynamic elastic response prosthetic feet: a pilot study," J Rehabil Res Dev, 27(4): p. 369-84 (1990).
Torburn et al., "Energy expenditure during ambulation in dysvascular and traumatic below-knee amputees: a comparison of five prosthetic feet," J Rehabil Res Dev, 32(2): p. 111-9 (1995).
Tseng et al., "Trends in initial lower extremity amputation rates among Veterans HealthAdministration health care System users from 2000 to 2004," Diabetes Care 34(5 p. 1157-63 (2011).
Tseng et al., "Evaluation of regional variation in total, major, and minor amputation rates in a national health-care system," International Journal for Quality in Health Care 19(6): p. 368-376 (2007).
Turner et al., "Suicidal Ideation among Individuals with Dysvascular Lower Extremity Amputation," Arch Phys Med Rehabil 2015. 96: p. 1404-10 (2015).
Turner et al., "Prevalence and 1-year course of alcohol misuse and smoking in persons with lower extremity amputation as a result of peripheral arterial disease," Am J Phys Med Rehabil, 93(6): p. 493-502 (2014).
Twiste et al., "Transverse rotation and longitudinal translation during prosthetic gait—a literature review," Journal of Rehabilitation Research and Development Jan.-Feb.;40(1):9-18 (2003).
Underwood et al., "A Comparison of Two Prosthetic Feet on the Multi-Joint and Muli-Plane Kinetic Gait Compensations in Individuals with a Unilateral Trans-Tibial Amputation," Clinical Biomechanic vol. 19, Issue 6, 609-616 (2004).
Unhelkar et al., "Human-robot co-navigation using anticipatory indicators of human walking motion," IEEE International Conference on Robotics and Automation (ICRA), p. 6183-6190 (2015).
Unwin et al., "Epidemiology of lower extremity amputation in centres in europe, north america and east asia," British Journal of Surgery, 87(3):328-337, (2000).
Van Der Linde et al., "A systematic literature review of the effect of different prosthetic components on human functioning with a lower-limb prosthesis," J Rehabil Res Dev, 41(4): p. 555-70 (2004).
Van Der Linden et al., "The biomechanical effects of the inclusion of a torque absorber on trans-femoral amputee gait, a pilot study," Prosthet Orthot Int, 26(1): p. 35-43 (2002).
Varol, "Multiclass real-time intent recognition of a powered lower limb prosthesis," IEEE Trans Biomed Eng 57(3): p. 542-51 (2010).
Veloso, "An agent-based simulation model for informed shared decision making in multiple sclerosis," Multiple sclerosis and related disorders, 2(4): p. 377-384 (2013).
Ventura et al., "Compensatory mechanisms of transtibial amputees during circular turning," Gait & posture, 34 (3):307-312, (2011).

(56) References Cited

OTHER PUBLICATIONS

Versluys et al., "Prosthetic feet: State-of-the-art review and the importance of mimicking human ankle-foot biomechanics," Disability & Rehabilitation: Assistive Technology, 4(2):65-75, (2009).
Von Elm et a., "The Strengthening the Reporting of Observational Studies in Epidemiology [STROBE] statement: guidelines for reporting observational studies," Gaceta Sanitaria, 22(2): p. 144-150 (2008).
Wasserteil-Smoller, "Mostly about quality of life. Biostatics and Epidemiology," New York: Springer-Verlag; p. 163-170 (1995).
Williams et al., "A Preliminary Study of Patient-Specific Mechanical Properties of Diabetic and Healthy Plantar Soft Tissue from Gated MRI," Proc Inst Mech Eng H, 231(7): p. 625-633 (2017).
Williams et al., "Changes in cognitive function from presurgery to 4 months postsurgery in individuals undergoing dysvascular amputation," Arch Phys Med Rehabil 95(4): p. 663-669 (2014).
Williams et al., "GPU based Path Integral Control with Learned Dynamics," Neural Information Processing Systems (NIPS) Montreal, CA (2014).
Williams et al., "Relationship Between Cognition and Functional Outcomes After Dysvascular Lower Extremity Amputation: A Prospective Study," Am J Phys Med Rehabil, 94(9): p. 707-717 (2015).
Williams et al., "The design and validation of a magnetic resonance imaging-compatible device for obtaining mechanical properties of plantar soft tissue via gated acquisition," Proc Inst Mech Eng H, 229(10): p. 732-42 (2015).
Williams et al., The role of expectations in pain after dysvascular lower extremity amputation. Rehabil Psychol 59 (4): p. 459-63 (2014).
Winter et al., "Biomechanical walking pattern changes in the fit and healthy elderly," Phys Ther, 70(6): p. 340-7 (1990).
Winter et al., "Biomechanics of below-knee amputee gait," Journal of biomechanics, 21(5):361-367, (1988).
Winter et al., "Measurement and reduction of noise in kinematics of locomotion," Journal of biomechanics, 7(2):157-159, (1974).
Witteman et al., "User-centered design and the development of patient decision aids: protocol for a systematic review," Systematic Reviews 4(11): p. 1-8 (2015).
Wright et al., "A comparison of different indices of responsiveness," J Clin Epidemiol 50(3): 239-46 (1997).
Xu et al., "Systematic review of concepts measured in individuals with lower limb amputation using the International Classification of Functioning, Disability and Health as a reference," Prosthet Orthot Int 35(3): 262-8 (2011).
Zatsiorsky et al., "In vivo body segment inertial parameters determination using a gamma-scanner method," Biomechanics of human movement: Applications in rehabilitation, sports and ergonomics, pp. 186-202, (1990).
The International Search Report (ISR) for PCT/US2017/036480 dated Aug. 7, 2017, pp. 1-3.
Written Opinion of the International Searching Authority for PCT/US2017/036480 dated Aug. 7, 2017, pp. 1-4.
AFHSC, Armed Forces Health Surveillance Center: Amputations of upper and lower extremities, active and reserve components, U.S. Armed Forces, 2000-2011, Med Surveillance Monthly Rep 19(6): p. 2-6 (2012).
ASTM International. ASTM D 72641 D7264M-15, "Standard test method for flexural properties of polymer matrix composite materials," 10 pages (2015).
Au et al., "Biomechanical design of a powered ankle-foot prosthesis. in Rehabilitation Robotics," 2007. ICORR 2007. IEEE 10th International Conference on, pp. 298-303. IEEE, (2007).
Au et al., "Powered ankle-foot prosthesis for the improvement of amputee ambulation," In Engineering in Medicine and Biology Society Conf EMBS 2007. 29th Annual International Conference of the IEEE, pp. 3020-3026. IEEE (2007).
Au et al., "Powered ankle-foot prosthesis to assist level-ground and stair-descent gaits," Neural networks : the official journal of the International Neural Network Society, 21: p. 654-66 (2008).

Aubin et al., "Gait simulation via a 6-DOF parallel robot with iterative learning control," IEEE transactions on biomedical engineering, 55(3): p. 1237-40 (2008).
Aulivola et al., "Major lower extremity amputation: outcome of a modern series," Archives of Surgery,139(4): p. 395-399 (2004).
Barlett et al., "Reliability and Validity of Selected PROMIS Measures in People with Rheumatoid Arthritis," PLoS One, 10(9): p. e0138543 (2015).
Barnett et al., The axis of rotation at the ankle joint in man; its influence upon the form of the talus and the mobility of the fibula. Journal of Anatomy, 86(1): p. 1-9 (1952).
Belatti et al., "Declines in lower extremity amputation in the US Medicare population, 2000-2010," Foot Ankle Int 34 (7): p. 923-31 (2013).
Bell et al., "A comparison of the accuracy of several hip center location prediction methods," J Biomech, 23(6): p. 617-21 (1990).
Bell et al., "Prediction of hip joint centre location from external landmarks," Human Movement Science, 8(1): p. 3-16 (1989).
Bergelin et al., "Design of an active ankle-foot prosthesis utilizing a four-bar mechanism," Journal of Mechanical Design, 134(6):061004, (2012).
Blaya et al., "Adaptive control of a variable-impedance ankle-foot orthosis to assist drop-foot gait," Neural Systems and Rehabilitation Engineering, IEEE Transactions on, 12(1):24-31, (2004).
Bonomi et al., "Quality of life measurement: will we ever be satisfied?," J Clin Epidemiol 53(1): 19-23 (2000).
Brehaut et al., "Validation of a decision regret scale," Medical Decision Making, 23(4): p. 281-292 (2003).
Brogan et al., "Realistic human walking paths" Proceedings of the 16th International Conference on Computer Animation and Social Agents (CASA '03). 8 pages (2003).
Buckley et al., "Oxygen consumption during ambulation: comparison of using a prosthesis fitted with and without a tele-torsion device," Arch Phys Med Rehabil, 2002. 83(4): p. 576-80.
Burke et al., "Bone and joint changes in lower limb amputees," Ann Rheum Dis, 37(3): p. 252-4 (1978).
Camacho et al., "A three-dimensional, anatomically detailed foot model: a foundation for a finite element simulation and means of quantifying foot-bone position," J Rehabil Res Dev, 39(3): p. 401-10 (2002).
Cappozzo et al., "Surface-marker cluster design criteria for 3-D bone movement reconstruction. IEEE Trans Biomed Eng," 44(12): p. 1165-74 (Cappozzo, A., et al., Surface-marker cluster design criteria for 3-D bone movement reconstruction. IEEE Trans Biomed Eng, 44(12): p. 1165-74 (1997).
Caputo et al., "In vivo kinematics of the tibiotalar joint after lateral ankle instability," Am J Sports Med 37(11): p. 2241-8 (2009).
Cavanagh et al., "Treatment for diabetic foot ulcers," Lancet, 366(9498): p. 1725-35 (2005).
CDCP, National diabetes fact sheet: national estimates and general information on diabetes and prediabetes in the United States 2011, Atlanta, GA: U.S. Department of Health and Human Services, Centers for Disease Control and Prevention. 12 pages (2011).
Charles et al., "Self-reported use of shared decision-making among breast cancer specialists and perceived barriers and facilitators to implementing this approach," Health Expectations, 7(4): p. 338-348 (2004).
Chen et al., "Effects of internal stress concentrations in plantar soft-tissue—A preliminary three-dimensional finite clement analysis," Med Eng Phys 32(4): p. 324-31 (2010).
Cherelle et al., "The AMP-foot 2.0: Mimicking intact ankle behavior with a powered transtibial prosthesis," In Biomedical Robotics and Biomechatronics (BioRob) 2012 4th IEEE RAS & EMBS International Conference on, pp. 544-549. IEEE, (2012).
Cheung et al., "Effect of Achilles tendon loading on plantar fascia tension in the standing foot," Clin Biomech (Bristol, Avon), 2006. 21(2): p. 194-203 (2006).
Cho et al., "Gender differences in three dimensional gait analysis data from 98 healthy korean adults," Clinical biomechanics, 19(2):145-152, (2004).
Close er al., "The function of the subtalar joint," Clinical orthopaedics and related research, 50:159-180, (1967).

(56) References Cited

OTHER PUBLICATIONS

Cofré et al., Aging modifies joint power and work when gait speeds are matched. Gait Posture, 33(3): p. 484-9 (2011).
Cohen editor, "Statistical Power Analysis for the Behavioral Sciences." 2nd ed: Routledge; 579 pages (1988).
Committee on Quality Healthcare in America, Institute of Medicine, "Crossing the quality chasm: a new health system for the 21st Century." National Academy Press, Washington D.C. pp. 1-359 (2001).
Condie et al., "Lower limb prosthetic outcome measures: a review of the literature 1995 to 2005," J Prosthet Orthot 18(6):13-45 (2006).
Cruz et al., "Major lower extremity amputations at a Veterans Affairs hospital," Am J Surg 186(5): p. 449-54 (2003).
Czerniecki et al., "Joint moment and muscle power output characteristics of below knee amputees during running: the influence of energy storing prosthetic feet," J Biomech 24(1): p. 63-75 (1991).
Czernieckic et al., "Mobility changes in individuals with dysvascular amputation from thepresurgical period to 12 months postamputation," Archives of Physical Medicine & Rehabilitation 93(10): p. 1766-73.
Czernieckic et al., "The effect of rehabilitation in a comprehensive inpatient rehabilitation unit on mobility outcome after dysvascular lower extremity amputation, "Archives of Physical Medicine & Rehabilitation 93(8): p. 1384-91 (2012).
Davies et al., "Mobility outcome following unilateral lower limb amputation," Prosthet Orthot Int 27(3): 186-90 (2003).
De Leva, "Adjustments to zatsiorsky-seluyanov's segment inertia parameters," Journal of biomechanics, 29(9):1223-1230, (1996).
Deathe et al., "Selection of outcome measures in lower extremity amputation rehabilitation: ICF activities," Disabil Rehabil 31(18): 1455-73 (2009).
DeGroot et al., "The Dutch version of the Knee Injury and Osteoarthritis Outcome Score: a validation study," Health Qual Life Outcomes 6: 16 (2008).
Delbridge et al., "The aetiology of diabetic neuropathic ulceration of the foot," Br J Surg 72(1): p. 1-6. (1985).
Diftler et al., "Robonaut 2-the first humanoid robot in space," In Robotics and Automation (ICRA), 2011 IEEE International Conference, pp. 2178-2183. IEEE, (2011).
Dillingham et al, "Discharge destination after dysvascular lower-limb amputations." Archives of Physical Medicine & Rehabilitation 84(11): p. 1662-8 (2003).
Dillingham et al., "Limb amputation and limb deficiency: epidemiology and recent trends in the united states," Southern medical journal, 95(8):875-884, (2002).
Dillingham et al., "Use and satisfaction with prosthetic devices among persons with trauma-related amputations: a long-term outcome study," American Journal of Physical Medicine & Rehabilitation Aug.;80(8):563-71 (2001).
Dillingham, et al., "Reamputation, mortality, and health care costs among persons with dysvascular lower-limb amputations," Arch Phys Med Rehabil 86(3): p. 480-486 (2005).
Dillon et al., "Deliberations about the functional benefits and complications of partial foot amputation: do we pay need to the purported benefits at the expense of minimizing complications? ,"Arch Phys Med Rehabil 2013.94(8): p. 1429-1435.
Dillon et al., "Describing the outcomes of dysvascular partial foot amputation and how these compare to transtibial amputation: a systematic review protocol for the development of shared decision making resources," Systematic reviews, 4(1): p. 1. (2015).
Zhu et al., "On the design of a powered transtibial prosthesis with stiffness adaptable ankle and toe joints," Industrial Electronics, IEEE Transactions on, 61(9):4797-4807 (2014).
Ziegler et al., "Estimating the prevalence of limb loss in the United States: 2005 to 2050," Arch Phys Med Rehabil 89 (3): p. 422-9. (2008).
Zwipp et al., "Ankle joint biomechanics," Foot and Ankle Surgery, 1(1):21-27, (1994).

Dudek et al., "Skin problems in an amputee clinic." Am J Phys Med Rehabil, 85(5): p. 424-9 (2006).
Dul et al., "A kinematic model of the human ankle" Journal of Biomedical Engineering, 7: p. 137-143 (1985).
Eberhart, "Fundamental studies of human locomotion and other information relating to design of artificial limbs," Prosthetic Devices Research Project, College of Engineering University of California: Berkeley. p. 4-6. (1947).
Ehde et al., "Back pain as a secondary disability in persons with lower limb amputations," Arch Phys Med Rehabil, 82 (6): p. 731-4 (2001).
Ehde et al., "Chronic phantom sensations, phantom pain, residual limb pain, and other regional pain after lower limb amputation,"(2000) Archives of Physical Medicine and Rehabilitation Aug.;81(8):1039-44 (2000).
Eijk et al., "Geriatric rehabilitation of lower limb amputees: a multicenter study," Disabil Rehabil 34(2): 145-50 (2012).
Elo et al., "The qualitative content analysis process," J Adv Nurs, 62(1): p. 107-15 (2008).
Engkasan et al., "Who decides? A qualitative study on the decisional roles of patients, their caregivers and doctors on the method of bladder drainage after spinal cord injury," Spinal cord, 53(2): p. 130-134 (2015).
English et al., "Establishment of consistent gait after fitting of new components," Journal of Rehabilitation Research and Development, 32(1): 32-35, (1995).
Erdemie et al., "An inverse finite-element model of heel-pad indentation," J Biomech, 39(7): p. 1279-86 (2006).
Feinglass et al., "Rates of lower-extremity amputation and arterial reconstruction in the united states, 1979 to 1996," American Journal of Public Health, 89(8):1222-1227, (1999).
Fischer, "A Guide to U.S. Military Casualty Statistics: Operation Freedom's Sentinel, Operation Inherent Resolve, Operation New Dawn, Operation Iraqi Freedom, and Operation Enduring Freedom, in RS22542, Aug. 7, 2015," Congressional Research Service, Library of Congress. p. 7. (2015).
Fitzpatrick et al., "Evaluating patient-based outcome measures for use in clinical trials," Health Technol Assess 2 (14): 1-74 (1998).
Flick et al., "Comparison of human turning gait with the mechanical performance of lower limb prosthetic transverse rotation adapters," Prosthet Orthot Int, 29(1): p. 73-81 (2005).
Franchignoni et al., "Measuring mobility in people with lower limb amputation: Rasch analysis of the mobility section of the prosthesis evaluation questionnaire," J Rehabil Med 39(2): 138-44 (2007).
Franchignoni et al., "Reliability, validity, and responsiveness of the locomotor capabilities index in adults with lower-limb amputation undergoing prosthetic training," Arch Phys Med Rehabil 85(5): 743-8 (2004).
Fryar et al., "Anthropometric reference data for children and adults: United States, 2007-2010," Vital Health Stat 11. (252):1-48 (2012).
Gailey et al., "The amputee mobility predictor: an instrument to assess determinants of the lower-limb amputee's ability to ambulate," Arch Phys Med Rehabil 83(5): 613-27 (2002).
Gailey et al., "The effects of prosthesis mass on metabolic cost of ambulation in non-vascular trans-tibial amputees," Prosthet Orthot Int, 21(1): p. 9-16 (1997).
Gallagher et al., "The Trinity Amputation and Prosthesis Experience Scales and quality of life in people with lower-limb amputation," Arch Phys Med Rehabil 85(5): 730-6 (2004).
Gardner et al., "Gait biomechanics of a second generation unstable shoe," J Appl Biomech, 30(4): p. 501-7 (2014).
Gauthier-Gagnon et al., "Enabling factors related to prosthetic use by people with transtibial and transfemoral imputation," Arch Phys Med Rehabil 80(6): 706-13 (1999).
Gauthier-Gagnon et al., "Prosthetic profile of the amputee questionnaire: validity and reliability," Arch Phys Med Rehabil 75(12): 1309-14 (1994).
Gauthier-Gagnon et al., "The Locomotor Capabilities Index: content validity," JRehabil Outcomes Measurement 2 (4): 40-6 (1998).
Gefen et al., "Plantar soft tissue loading under the medial metatarsals in the standing diabetic foot," Med Eng Phys, 25(6): p. 491-9 (2003).

(56) References Cited

OTHER PUBLICATIONS

Geiss et al., "Prevalence and incidence trends for diagnosed diabetes among adults aged 20 to 79 years, United States, 1980-2012," JAMA, 312(12): p. 1218-26 (2014).
Genin et al., "Effect of speed on the energy cost of walking in unilateral traumatic lower limb amputees," Eur J Appl Physiol 103(6): p. 655-63.
Glaister et al., "A mechanical model of the human ankle in the transverse plane during straight walking: implications for prosthetic design," Journal of biomechanical engineering, 131(3):034501, (2009).
Glaister, et al., Video task analysis of turning during activities of daily living. Gait Posture, 25(2): p. 289-94 (2007).
Gorges, "Controlled coronal stiffness prosthetic ankle for improving balance on uneven terrain," Master's thesis, University of Washington, 67 pages (2013).
Goujon et al., "A functional evaluation of prosthetic foot kinematics during lower-limb amputee gait," Prosthetics and orthotics international, 30(2):213-223, (2006).
Gould et al., "Epidemiological survey of foot problems in the continental United States: 1978-1979," Foot Ankle 1(1): p. 8-10 (1980).
Grimmer et al., "Stiffness adjustment of a series elastic actuator in a knee prosthesis for walking and running: the trade-off between energy and peak power optimization," In Intelligent Robots and Systems (IROS), 2011 IEEE/RSJ International Conference on, pp. 1811-1816. IEEE, (2011).
Guyatt et al., "Health status, quality of life, and the individual." JAMA 272(8):630-1 (1994).
Hack et al., "Do patients benefit from participating in medical decision making? Longitudinal follow-up of women with breast cancer," Psycho-Oncology, 15(1): p. 9-19 (2006).
Hafner, "Clinical prescription and use of prosthetic foot and ankle mechanisms: A review of the literature," Journal of Prosthetics and Orthotics 17(4S): p. S5-S11 (2005).
Hafner et al., "Energy storage and return prostheses: does patient perception correlate with biomechanical analysis?," Clin Biomech (Bristol, Avon), 17(5): p. 325-44 (2002).
Hagberg et al., "Consequences of non-vascular trans-femoral amputation: a survey of quality of life, prosthetic use and problems," Prosthetics and Orthotics International Dec.;25(3):186-94 (2001).
Hansen et al., "Effective rocker shapes used by able-bodied persons for walking and fore-aft swaying: Implications for design of ankle—foot prostheses,"Gait & posture, 32(2):181-184, (2010).
Hansen et al., "The human ankle during walking: implications for design of biomimetic ankle prostheses," Journal of biomechanics, 37(10):1467-1474, (2004).
Hanspal et al., "Assessment of cognitive and psychomotor function and rehabilitation of elderly people with prostheses," BMJ1302 (1991).
Hargrove et al., "Robotic Leg Control with EMG Decoding in an Amputee with Nerve Transfers," New England Journal of Medicine, p. 1237-1242 (2013).
Haywood, "Patient-reported outcome: Measuring what matters or just another paper exercise?," Musculoskeletal care 2006; 4(2): 63-6.
Hebert et al., "Outcome measures in amputation rehabilitation: ICF body functions," Disabil Rehabil 31(19): 1541-54 (2009).
Heinemann et al., "Development and measurement properties of the Orthotics and Prosthetics Users' Survey (OPUS): a comprehensive set of clinical outcome instruments," Prosthet Orthot Int 27(3): 191-206 (2003).
Hermodsson et al., Gait in male trans-tibial amputees: a comparative study with healthy subjects in relation to walking speedProsthetics and orthotics international, 18(2):68-77, (1994).
Herr er al.,Bionic ankle-foot prosthesis normalizes walking gait for persons with leg amputation, Proc Biol Sci 279 (1728): p. 457-64 (2012).
Hicks, "The mechanics of the foot: I. The joints." Journal of Anatomy, 87(Pt 4): p. 345-357 (1953).
Hitt et al., "An active foot-ankle prosthesis with biomechanical energy regeneration," Journal of medical devices, 4 (1):011003, (2010).
Houghton et a., "Rehabilitation after lower limb amputation: a comparative study of above-knee, through-knee and Gritti-Stokes amputations," Br J Surg 76(6): 622-4 (1989).

\* cited by examiner

PIVOT-FLEX FOOT

CROSS-REFERENCE TO RELATED APPLICATIONS

This application claims the benefit of the filing date of international PCT Application No. PCT/US2017/036480, filed Jun. 8, 2017 that in turn claims priority to U.S. Provisional Patent Application Ser. No. 62/347,415, filed Jun. 8, 2016, which are hereby incorporated by reference in their entirety.

GOVERNMENT RIGHTS

This invention was made with government support under Grant Nos. A9243C and I01 RX002456, awarded by the Department of Veterans Affairs. The government has certain rights in the invention.

BACKGROUND

Unless otherwise indicated herein, the materials described in this section are not prior art to the claims in this application and are not admitted to be prior art by inclusion in this section.

Amputees are prone to pain and injury caused by loads applied to the residual limb through the prosthetic socket, as well as through compensatory gait adaptations. One source of pain and discomfort is epidermoid cysts which occur where the skin of the residual limb rubs against the brim of the socket. These cysts often develop over years of prosthesis use, and can become painful enough to prevent use of the prosthesis. These and other skin problems are attributed to the shear stress and humidity seen by the skin of the residual limb of lower-limb prosthesis users. Shear stress has been shown to cause blisters, and is a primary cause of callosities and trophic ulcers. A major source of shear stress on the residual limb of amputees is transverse-plane torque. Transverse-plane torque is a normal part of walking in non-amputees and increases in the inside leg of a turn. Turning steps compose a large fraction of the steps of daily living. In non-amputees, transverse-plane torque is transmitted from the ground to the trunk through the bones and muscles of the leg. In amputees, the torque is transmitted from the prosthetic socket to the skin of the residual limb. Amputees experience less transverse-plane torque during walking than non-amputees, due to compensatory gait patterns. Prosthetic legs for trans-tibial amputees typically consist of a prosthetic foot which is connected by a rigid pylon to the socket which interfaces with the residual limb. Because rotation is not allowed between the foot and the socket, any rotation between the foot and the knee must occur at the knee or between the residual limb and the socket. Thus, amputees must either adopt a compensatory gait pattern with reduced transverse-plane rotation or accept sliding between the residual limb and the socket.

In addition to skin problems at the interface between the residual limb and the socket, prosthesis users also suffer from increased rates of musculoskeletal problems such as osteoarthritis and chronic back pain compared with non-amputees. Improving prosthesis comfort during walking could lead to a more symmetric weight distribution and decreased risk of osteoarthritis.

While the human ankle contains a complex set of joints that allows rotation in each of the sagittal, coronal, and transverse planes, conventional prosthetic feet are typically designed to provide rotation in the sagittal plane only. Split toe or other multiaxial feet can provide some coronal-plane motion. A transverse rotation adapter can be added in series with the prosthesis pylon. While transverse rotation adapters increase transverse-plane rotation and decrease peak joint torques in the transverse plane rotation, their stiffness cannot be adjusted by the user and if excessively compliant may reduce amputee dynamic stability. Therefore, an improved prosthesis to couple the sagittal plane motion to the transverse plane may be desired.

SUMMARY

Example devices described herein allow adaptation of a prosthetic foot in the medial-lateral direction, including pronation and supination of the prosthetic foot. The device described herein may mimic the functions of a normal foot by coupling a rotation of prosthetic foot with respect to the sagittal plane to a rotation of the prosthetic foot with respect to the transverse plane. The disclosed devices may improve walking, running, and other forms of bipedal motion for people with prosthetic feet. In particular, the disclosed devices may allow for reduced transverse-plane torque in the residual limb of the user. The disclosed devices may further help improve the gait of the user, thereby reducing musculoskeletal problems of the user. Robotic prostheses may also benefit from the mechanical adaptations of the invention to make them more versatile and functional.

Thus, in one aspect, a prosthetic device is provided including (a) an ankle component, (b) a foot component coupled to the ankle component, wherein the foot component has a longitudinal length extending at least partially along a sagittal plane of a user when the prosthetic device is in use, wherein the foot component has a thickness extending at least partially along a transverse plane of a user when the prosthetic device is in use, and (c) a coupling mechanism positioned between the foot component and the ankle component, wherein the coupling mechanism couples a rotation of the foot component with respect to the sagittal plane to a rotation of the foot component with respect to the transverse plane.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means+/−5%.

As used herein, "sagittal plane" means a plane that is parallel to a length of a prosthetic foot, dividing the prosthetic foot into left and right portions.

As used herein, "coronal plane" means a plane that is perpendicular to a length of a prosthetic foot, dividing the prosthetic foot into back and front portions.

As used herein, "transverse plane" means a plane that is parallel to a width of a prosthetic foot, dividing the prosthetic foot into top and bottom portions.

As used herein, "coupling ratio" means a ratio between rotation of the prosthetic foot in the sagittal plane to rotation of the prosthetic foot in the transverse plane. For example, if a rotation of three degrees in the sagittal plane causes a rotation of one degree in the transverse plane, then the prosthetic foot has a coupling ratio of 3:1.

The human ankle is a complex mechanism that does not behave like a simple hinge. Instead, rotations in each of the sagittal, coronal, and transverse planes are allowed and coupled together. In particular, the axis of rotation of the talocrural joint during ankle dorsiflexion is inclined downwards and laterally relative to horizontal, and the rotation ranges from 10 to 26 degrees among individuals. This rotation couples dorsiflexion with internal rotation of the shank relative to the foot, a feature which is not replicated in traditional prosthetic feet and ankles. The device described herein may mimic the functions of a normal foot by coupling a rotation of prosthetic foot with respect to the sagittal plane to a rotation of the prosthetic foot with respect to the transverse plane, as described in more detail with reference to the figures below. The disclosed devices may improve walking, running, and other forms of bipedal motion for people with prosthetic feet.

Figure 1:
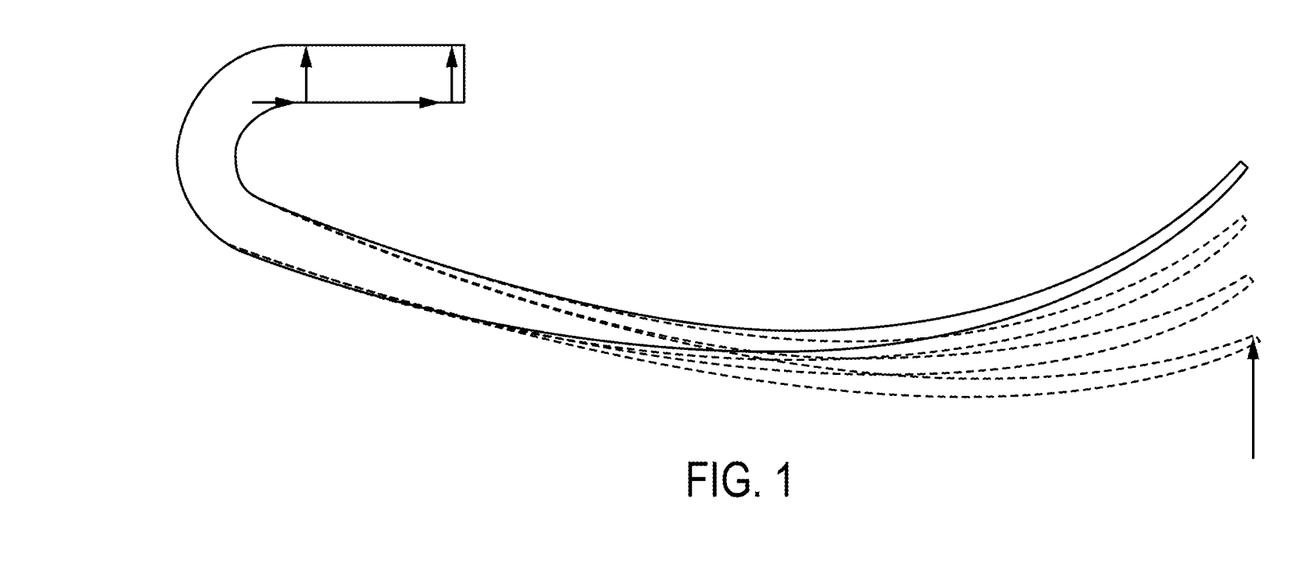
FIG. 1 is a side cross-section view of an example cantilever leaf spring with a vertical force at the toe, according to an example embodiment.

Modern prosthetic feet are typically composed of a carbon-fiber composite cantilever leaf spring (called the keel) enclosed in a cosmetic silicone foot shell. The cosmetic foot shell is very flexible and the mechanical behavior of the foot is determined by the shape of the composite leaf spring. The typical keel has a non-uniform rectangular cross-section with a large width-to-thickness ratio ranging from 2:1 to 10:1. Because the cantilever leaf spring is much more flexible in the sagittal plane than in the other planes, the rotation of the foot is effectively confined to the sagittal plane. FIG. 1 shows a schematic representation of the sagittal-plane rotation of an example cantilever leaf spring. Because the stiffness of the cantilever leaf spring is distributed, there is no single axis of rotation. Instead, the effective axis of rotation moves forward during the gait cycle as the center of pressure progresses from the heel to the toe. Additionally, many keels are split along the sagittal plane. This allows differential deflection between the medial and lateral cantilever leaf springs, which emulates coronal-plane rotation. However, this does not translate to a rotation with respect to the transverse plane.

Figure 2:
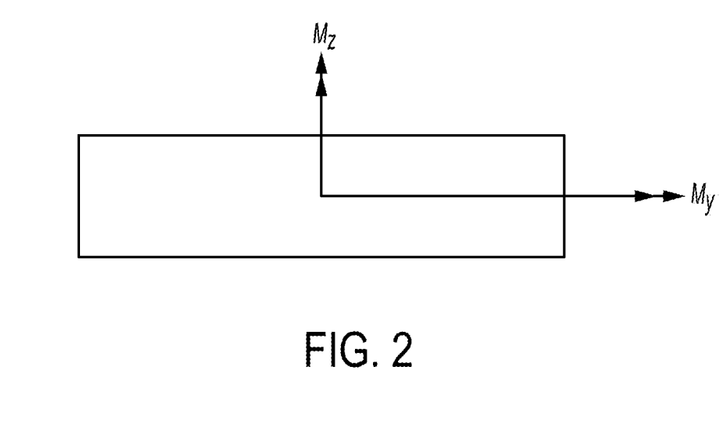
FIG. 2 is a transverse cross-sectional view of a cantilever leaf spring aligned with the sagittal plane, according to an example embodiment.

A cantilever leaf spring can provide coupling between flexure in the sagittal and transverse planes by tailoring the cross-section of the cantilever leaf spring. This can be seen by considering a rectangular cross-section subject to a bending moment $M_y$ in the sagittal plane. If the principal moments of inertia are aligned with the sagittal plane moment as shown in the transverse cross-sectional view of the cantilever leaf spring in FIG. 2, the deflection of the beam obeys:

$$\frac{\partial^2 w_z}{\partial x^2} = \frac{M_y}{EI_{zz}}, \frac{\partial^2 w_y}{\partial x^2} = -\frac{M_z}{EI_{yy}} = 0 \quad (1)$$

where E is the modulus of elasticity of the material, $w_y$ and $w_z$ are the deflections in the y and z directions, respectively, and $I_{yy}$ and $I_{zz}$ are the second moments of area of the cross-section.

Figure 3:
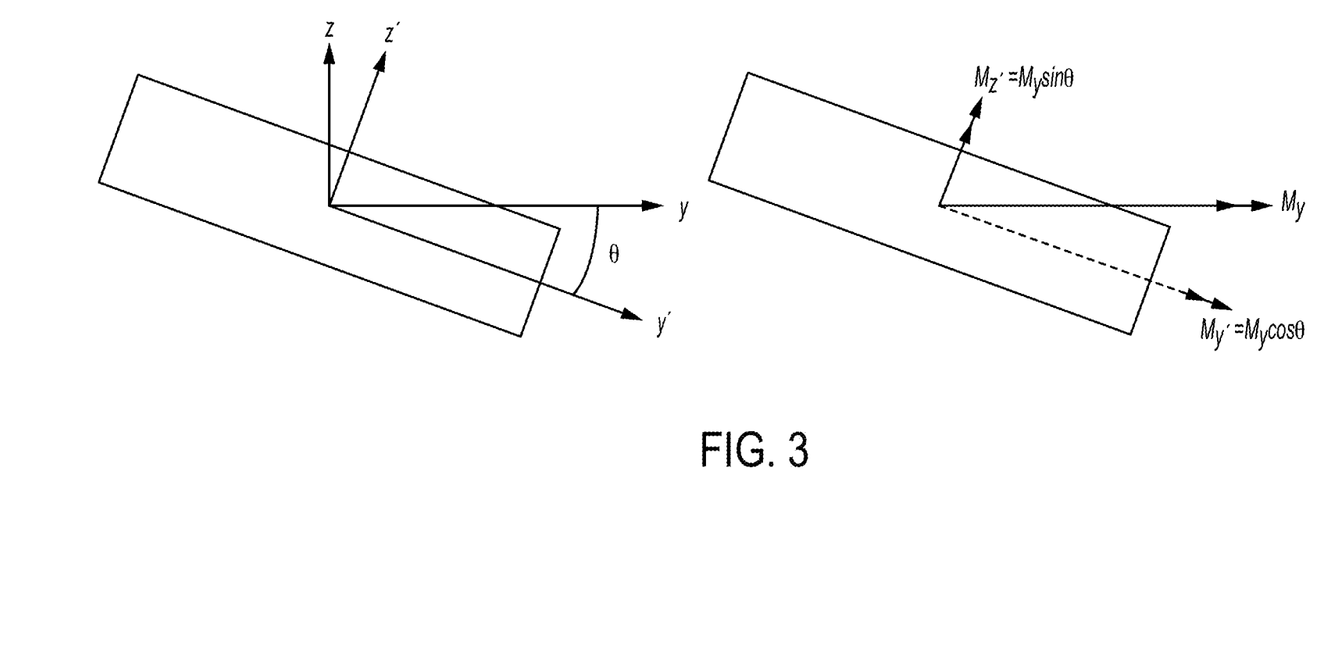
FIG. 3 is a transverse cross-sectional view of a cantilever leaf spring misaligned with the sagittal plane, according to an example embodiment.

If the transverse cross-section of the cantilever leaf spring is rotated as in FIG. 3, a sagittal plane bending moment results in deflections in both the y and z directions:

$$\frac{\partial^2 w_z}{\partial x^2} = \frac{M_y \cos^2\theta}{EI_{zz}} + \frac{M_y \sin^2\theta}{EI_{yy}}, \frac{\partial^2 w_y}{\partial x^2} = \frac{M_y \cos\theta \sin\theta}{EI_{zz}} - \frac{M_y \cos\theta \sin\theta}{EI_{yy}} \quad (2)$$

The ratio of the deflections is:

$$\frac{\frac{\partial^2 w_y}{\partial x^2}}{\frac{\partial^2 w_x}{\partial x^2}} = \frac{\cos\theta \sin\theta \left(1 - \frac{I_{zz}}{I_{yy}}\right)}{\cos^2\theta + \sin^2\theta \frac{I_{zz}}{I_{yy}}} = \frac{\tan\theta \left(1 - \frac{I_{zz}}{I_{yy}}\right)}{1 + \tan^2\theta \frac{I_{zz}}{I_{yy}}} \quad (3)$$

For a rectangular cross-section, $$\frac{I_{zz}}{I_{yy}} = \frac{t^2}{w^2},$$

where t is the thickness and w is the width of the cross-section. If the rotation angle is constant and the thickness is small relative to the width, then $$\frac{I_{zz}}{I_{yy}} \ll 1 \text{ and } \frac{w_y}{w_z} \approx \tan(\theta).$$

Thus, coupling between sagittal-plane and transverse-plane rotation can be achieved in a cantilever beam with a rectangular cross-section if the cross-section is misaligned with the sagittal plane.

Figure 4:
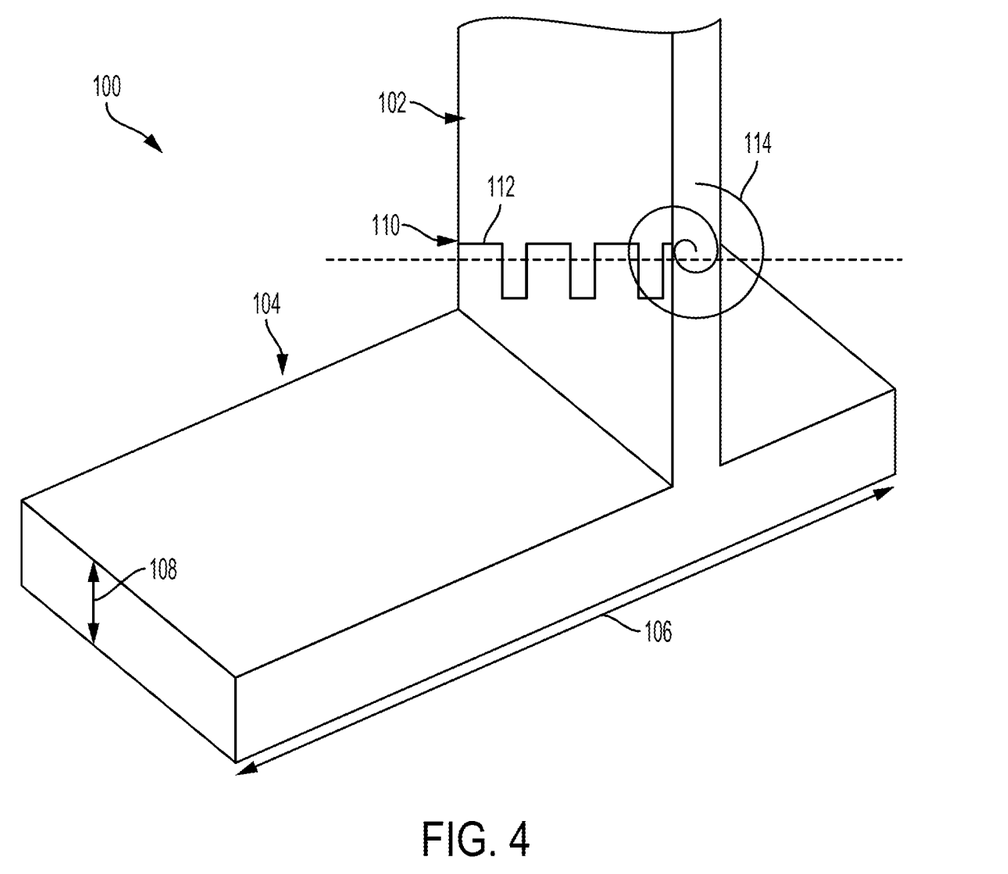
FIG. 4 is a perspective view of an example prosthetic foot, according to an example embodiment.

Thus, in a first aspect, FIG. 4 illustrates an example prosthetic device 100 in accordance with one embodiment of the invention. As shown in FIG. 4, the prosthetic device 100 may include an ankle component 102, and a foot component 104 coupled to the ankle component 102. The ankle component 102 and the foot component may be unitary components, or they may be separate components that are coupled together. The foot component 104 has a longitudinal length 106 extending at least partially along a sagittal plane of a user when the prosthetic device 100 is in use. In addition, the foot component 104 has a thickness 108 extending at least partially along a transverse plane of a user when the prosthetic device 100 is in use. The prosthetic device 100 may also include a coupling mechanism 110 positioned between the foot component 104 and the ankle component 102. The coupling mechanism 110 couples a rotation of the foot component 104 with respect to the sagittal plane to a rotation of the foot component 104 with respect to the transverse plane. A coupling ratio of the rotation of the foot component 104 with respect to the sagittal plane to the rotation of the foot component 104 with respect to the transverse plane ranges from about 2:1 to about 6:1. The coupling mechanism 110 is configured to cause the foot component 104 to rotate away from a midline of the user when the prosthetic device 100 is in use.

The coupling mechanism 110 may take a variety of forms. In one example, as shown in FIG. 4, the coupling mechanism 110 comprises a hinge 112 positioned between the ankle component 102 and the foot component 104. As shown in FIG. 4, the hinge 112 is positioned at an offset angle with respect to the sagittal plane of a user. The offset angle of the hinge 112 ranges from about 5 degrees to about 30 degrees. As such, the hinge 112 causes the foot component 104 to move up and down as well as in and out, thereby coupling a rotation of the foot component 104 with respect to the sagittal plane to a rotation of the foot component 104 with respect to the transverse plane. The hinge 112 may further include a torsion spring 114 configured to bias the hinge 112 to a closed position.

Figure 5:
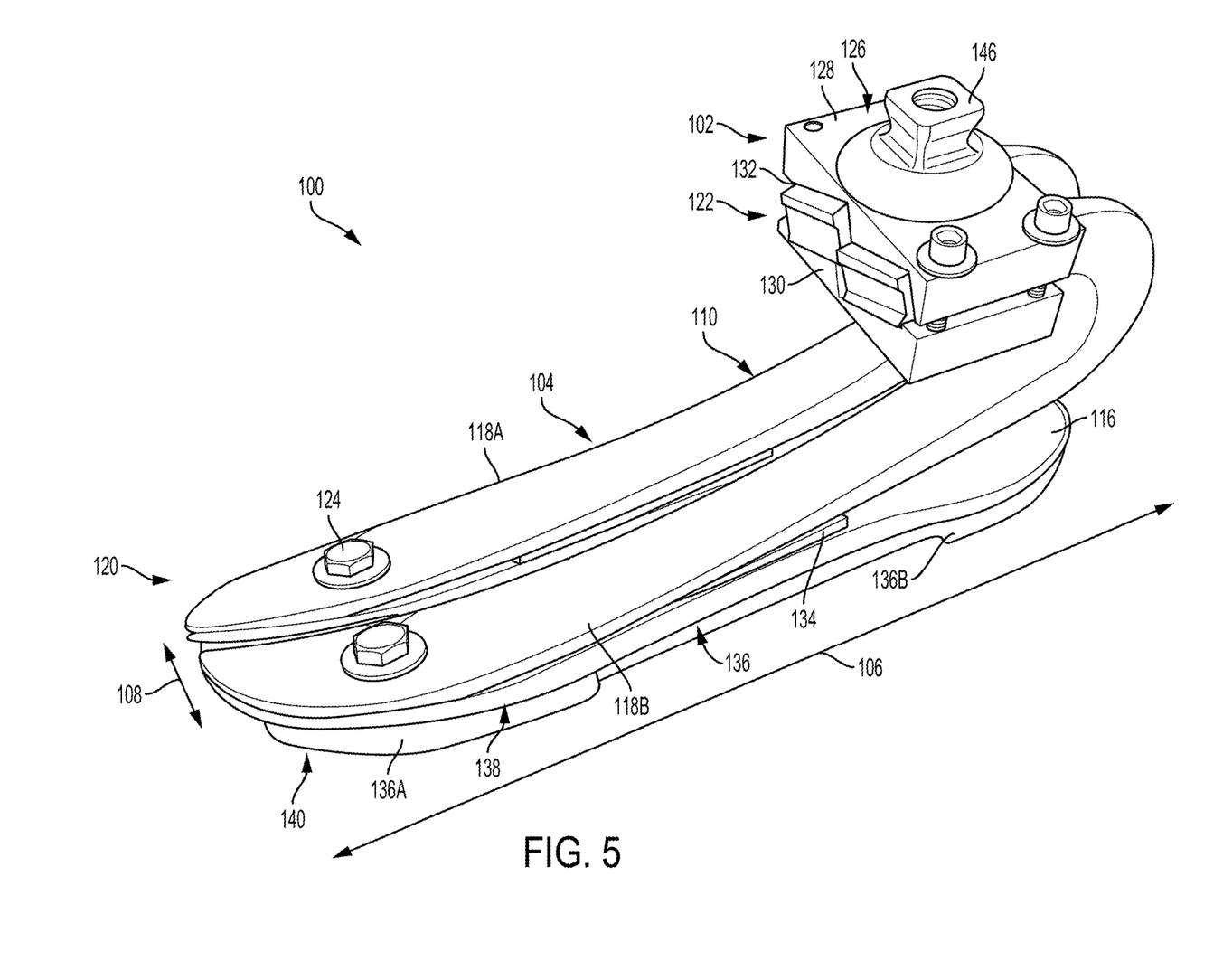
FIG. 5 is a perspective view of another example prosthetic foot, according to an example embodiment.
Figure 6:
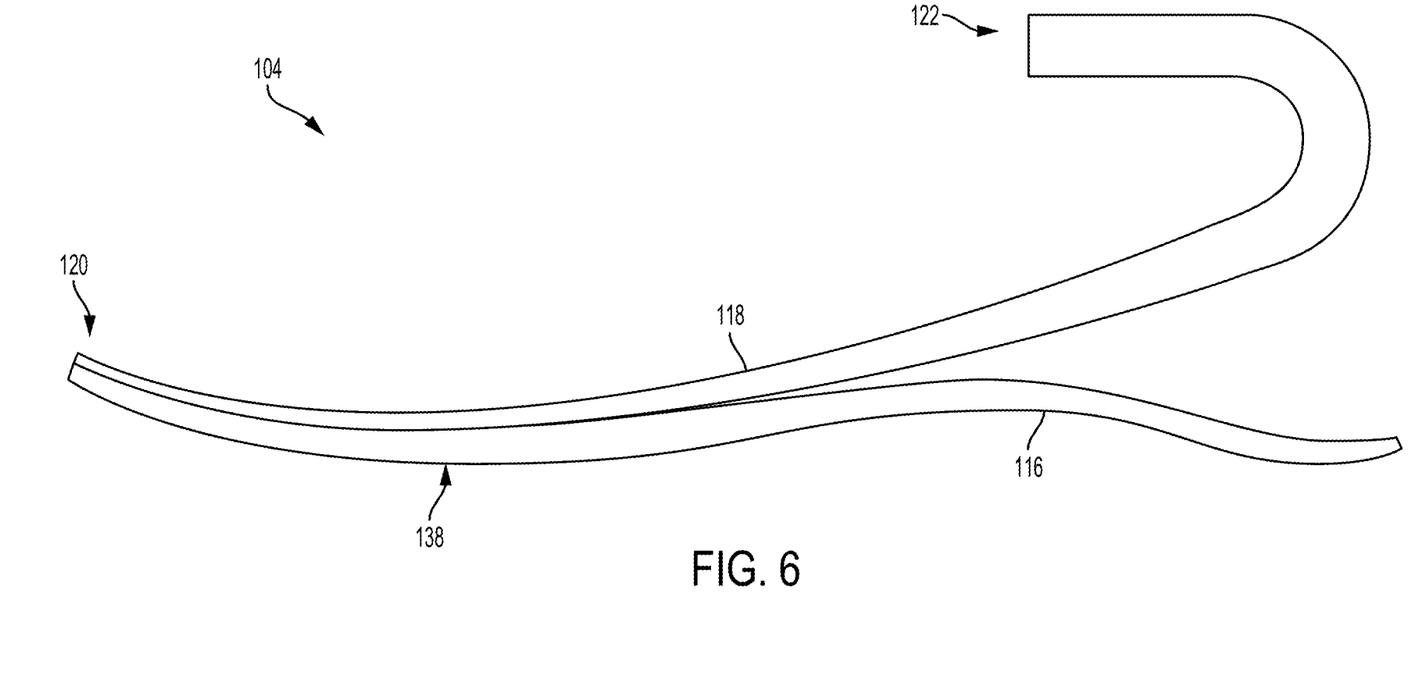
FIG. 6 is a side cross-section view of a lower cantilever leaf spring and an upper cantilever leaf spring of the prosthetic foot of FIG. 5, according to an example embodiment.

In another example, as shown in FIG. 5, the foot component 104 comprises a lower cantilever leaf spring 116. In such an embodiment, the coupling mechanism 110 comprises one or more upper cantilever leaf springs 118 each having a transverse cross-section defined by a width extending at least partially along a coronal plane of a user when in use and a thickness extending at least partially along the transverse plane of a user when in use. FIG. 6 illustrates a side cross-section view of the lower cantilever leaf spring 116 and an upper cantilever leaf spring of the one or more upper cantilever leaf springs 118. The transverse cross-section of the one or more upper cantilever leaf springs 118 may take a variety of forms.

In general, the transverse cross-section of the one or more upper cantilever leaf springs 118 may be any shape as long as (i) the stiffness in the coronal plane and the transverse plane are much different (e.g., the one or more upper cantilever leaf springs 118 are much stiffer in one direction than in the other direction), and (ii) the minor principal axis of the one or more upper cantilever leaf springs 118 is misaligned with the sagittal plane. In one example, the transverse cross-section is L-shaped. In another example, the transverse cross-section is triangular-shaped.

Figure 7:
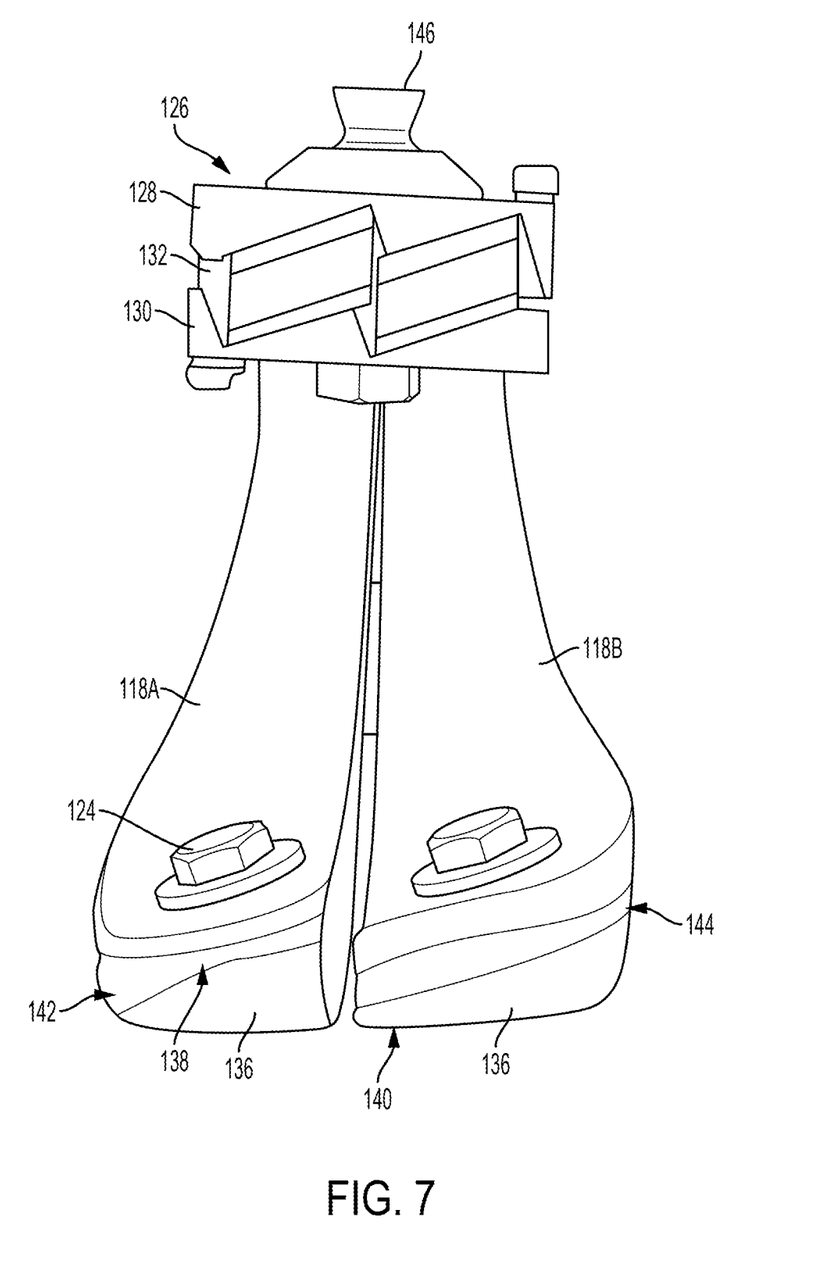
FIG. 7 is a front view of the example prosthetic foot of FIG. 5, according to an example embodiment.

In yet another example, as shown in FIGS. 5-7, the transverse cross-section is rectangular-shaped. In such an example, a ratio of the width to the thickness of the one or more upper cantilever leaf springs may range from about 2:1 to about 20:1. As shown in FIG. 7, the transverse cross-section of the one or more upper cantilever leaf springs 118 are each misaligned with the sagittal plane by a rotation angle such that if the foot component 104 is subjected to a bending moment along the sagittal plane, the sagittal plane bending moment will simultaneously deflect the foot component 104 along both the sagittal plane and the transverse plane. The rotation angle of the one or more upper cantilever leaf springs 118 with respect to the sagittal plane may range from about 0 degrees to about 30 degrees. In one example, the rotation angle is constant along the longitudinal length of the foot component. In another example, the rotation angle varies along the longitudinal length of the foot component.

In one embodiment, as shown in FIG. 5, the lower cantilever leaf spring 116 is coupled to a first end 120 of the one or more upper cantilever leaf springs 118, and the ankle component 102 is coupled to a second end 122 of the one or more upper cantilever leaf springs 118. Further, as shown in FIG. 5, the first end 120 of the one or more upper cantilever leaf springs 118 may be coupled to the lower cantilever leaf spring 116 via a mechanical fastener 124. The mechanical fastener 124 may comprise a nut and bolt, a screw, or a rivet, as non-limiting examples. Other mechanical fasteners are possible as well. In another embodiment, an adhesive may be used to secure the first end 120 of the one or more upper cantilever leaf springs 118 to the lower cantilever leaf spring 116. In another embodiment, the one or more upper cantilever leaf springs 118 and the lower cantilever leaf springs 116 may be manufactured as one continuous piece, such that the first end 120 of the one or more upper cantilever leaf springs 118 is secured to the lower cantilever leaf spring 116 during manufacturing.

In one embodiment, as shown in FIG. 5 and FIG. 7, the ankle component 102 is coupled to the second end 122 of the one or more upper cantilever leaf springs 118 via a bracket 126. The bracket 126 may include an upper portion 128 removably coupled to a lower portion 130. The upper portion 128 and the lower portion 130 may each include one or more angled cutouts 132 configured to receive the one or more upper cantilever leaf springs 118 at the rotation angle. As such, the bracket 126 may help maintain the rotation angle of the one or more upper cantilever leaf springs 118 such that the transverse cross-section of the one or more upper cantilever leaf springs 118 are each misaligned with the sagittal plane.

In one example, the one or more upper cantilever leaf springs 118 comprises a single leaf spring. In another example, the one or more upper cantilever leaf springs 118 comprises a plurality of leaf springs, such as three or four leaf springs. In yet another example, as shown in FIGS. 5 and 7, the one or more upper cantilever leaf springs 118 comprises two leaf springs 118A, 118B. In such an example, as shown in FIG. 7, each of the two leaf springs 118A, 118B are misaligned with the sagittal plane by the rotation angle.

In another example, as shown in FIG. 5, the prosthetic foot 100 may further include an elastomer material 134 positioned between the lower cantilever leaf spring 116 and the one or more upper cantilever leaf springs 118. The elastomer material 134 may comprise a foam material, rubber, neoprene, or silicone, as non-limiting examples. The elastomer material 134 may provide a cushioning and dampening between the lower cantilever leaf spring 116 and the one or more upper cantilever leaf springs 118.

In another embodiment, as shown in FIGS. 5 and 7, the prosthetic device 100 may include one or more wedges 136 coupled to a bottom surface 138 of the lower cantilever leaf spring 116. In one particular example, as shown in FIG. 5, the one or more wedges 136 comprise a toe wedge 136A positioned under a front portion of the lower cantilever leaf spring 116 and a heel wedge 136B positioned under a rear portion of the lower cantilever leaf spring 116. In another example, the one or more wedges 136 comprises a single wedge extending a length of the foot component 104. As shown in FIG. 7, a lateral border 142 of the foot component 104 may be lower than a medial border 144 of the foot component 104. As such, the one or more wedges 136 may be shaped and angled such that a bottom surface 140 of the one or more wedges 136 is parallel to a ground surface when in use. The one or more wedges 136 are configured to distribute the load from the foot component 104 to the ground surface.

The lower cantilever leaf spring 116 may comprise a first material, the one or more upper cantilever leaf springs 118 may comprise a second material, and the one or more wedges 136 may comprise a third material that is different than the first material and the second material. In one example, the first material is the same as the second material such that the lower cantilever leaf spring 116 and the one or more upper cantilever leaf springs 118 comprise the same material. In another example, the first material is different than the second material such that the lower cantilever leaf spring 116 and the one or more upper cantilever leaf springs 118 comprise different materials. In one example, the first material of the lower cantilever leaf spring 116 comprises a stiffer material than the second material of the one or more upper cantilever leaf springs 118. In another example, the first material of the lower cantilever leaf spring 116 comprises a more compliant material than the second material of the one or more upper cantilever leaf springs 118.

The first material may comprise carbon fiber, carbon fiber composite, high density nylon material, steel, aluminum, fiberglass, or a sandwich panel with carbon fiber or fiberglass outer layers around a foam, honeycomb, or balsa core. The second material may comprise carbon fiber, carbon fiber composite, high density nylon material, steel, aluminum, fiberglass, or a sandwich panel with carbon fiber or fiberglass outer layers around a foam, honeycomb, or balsa core. The third material may comprise nylon, ABS, PLA, poylethylene, carbon fiber, or a fiberglass composite.

Figure 8:
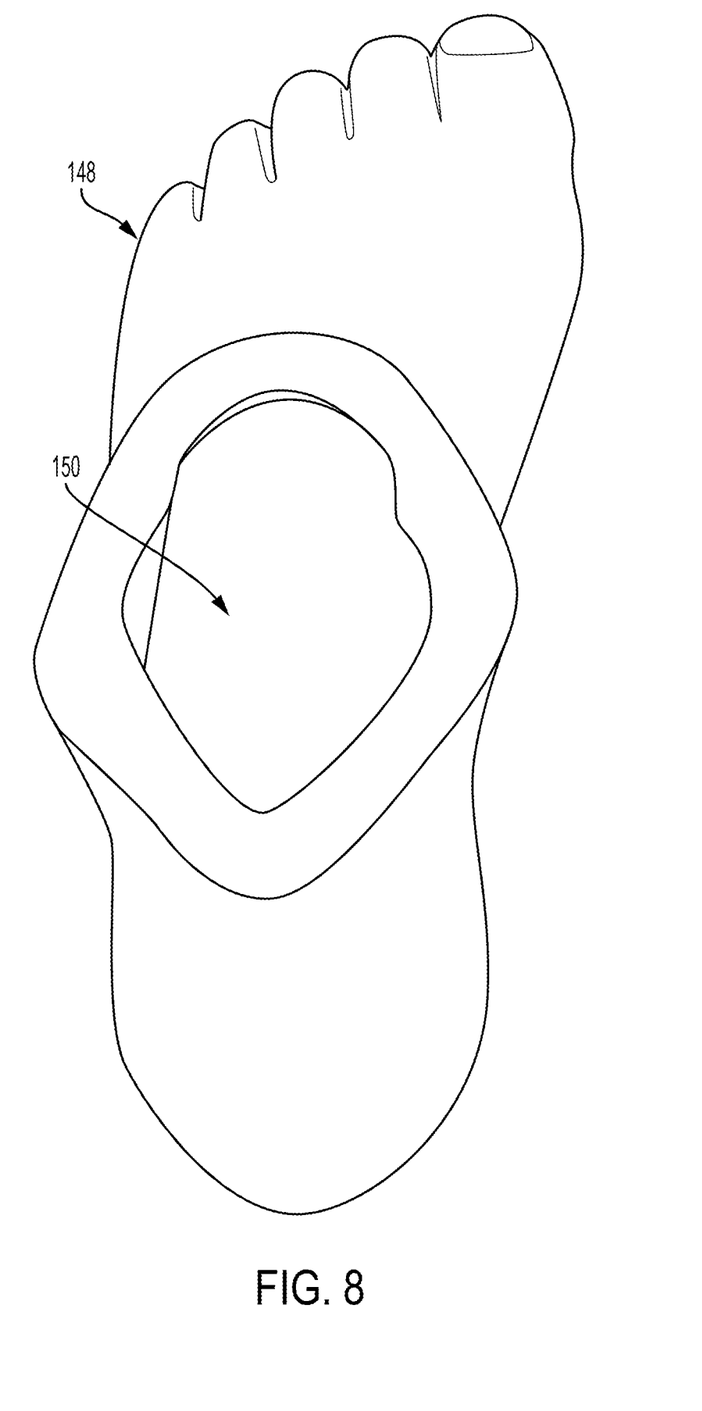
FIG. 8 is a top view of an example cosmetic foot shell, according to an example embodiment.

As shown in FIG. 5, the prosthetic device 100 may further include a pyramid adapter 146 coupled to the ankle component 102. The pyramid adapter 146 is configured to be coupled to a prosthetic limb of a user. Further, as shown in FIG. 8, the prosthetic device 100 may further include a cosmetic foot shell 148 configured and arranged for disposing over at least a portion of the foot component 104. The cosmetic foot shell 148 may include a cavity 150 into which the foot component 104 may be positioned.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A prosthetic device, comprising:
   an ankle component;
   a foot component coupled to the ankle component, wherein the foot component has a longitudinal length configured to extend at least partially along a sagittal plane of a user when the prosthetic device is in use, wherein the foot component has a thickness configured to extend at least partially along a transverse plane of the user when the prosthetic device is in use, and wherein the foot component comprises a lower cantilever leaf spring; and
   a coupling mechanism positioned between the foot component and the ankle component, wherein the coupling mechanism couples a rotation of the foot component with respect to the sagittal plane to a rotation of the foot component with respect to the transverse plane, wherein the coupling mechanism comprises one or more upper cantilever leaf springs each having a transverse cross-section defined by a width configured to extend at least partially along a coronal plane of the user when the prosthetic device is in use and a thickness configured to extend at least partially along the transverse plane of the user when the prosthetic device is in use, and wherein the transverse cross-section of the one or more upper cantilever leaf springs are each configured to be misaligned with the sagittal plane by a rotation angle when the prosthetic device is in use such that if the foot component is subjected to a bending moment along the sagittal plane, the sagittal plane bending moment will simultaneously deflect the foot component along both the sagittal plane and the transverse plane.

2. The prosthetic device of claim 1, wherein the prosthetic device further comprises a pyramid adapter coupled to the ankle component, wherein the pyramid adapter is configured to be coupled to a prosthetic limb.

3. The prosthetic device of claim 1, wherein a coupling ratio of the rotation of the foot component with respect to the sagittal plane to the rotation of the foot component with respect to the transverse plane ranges from 2:1 to 6:1.

4. The prosthetic device of claim 1, wherein the transverse cross-section is L-shaped, triangular-shaped or rectangular-shaped.

5. The prosthetic device of claim 1, wherein a ratio of the width to the thickness of the one or more upper cantilever leaf springs ranges from 2:1 to 20:1.

6. The prosthetic device of claim 1, wherein the rotation angle is constant along the longitudinal length of the foot component, varies along the longitudinal length of the foot component or the rotation angle ranges from 0 degrees to 30 degrees.

7. The prosthetic device of claim 1, wherein the lower cantilever leaf spring is coupled to a first end of the one or more upper cantilever leaf springs, and wherein the ankle component is coupled to a second end of the one or more upper cantilever leaf springs.

8. The prosthetic device of claim 7, wherein the first end of the one or more upper cantilever leaf springs are coupled to the lower cantilever leaf spring via a mechanical fastener.

9. The prosthetic device of claim 7, wherein the ankle component is coupled to the second end of the one or more upper cantilever leaf springs via a bracket.

10. The prosthetic device of claim 9, wherein the bracket includes an upper portion removably coupled to a lower portion, and wherein the upper portion and the lower portion each include one or more angled cutouts configured to receive the one or more upper cantilever leaf springs at the rotation angle.

11. The prosthetic device of claim 1, wherein the one or more upper cantilever leaf springs comprises two leaf springs, wherein each of the two leaf springs are configured to be misaligned with the sagittal plane by the rotation angle when the prosthetic device is in use.

12. The prosthetic device of claim 1, wherein the prosthetic device further comprises an elastomer material positioned between the lower cantilever leaf spring and the one or more upper cantilever leaf springs.

13. The prosthetic device of claim 1, wherein the prosthetic device further comprises one or more wedges coupled to a bottom surface of the lower cantilever leaf spring.

14. The prosthetic device of claim 13, wherein the one or more wedges comprise a toe wedge positioned under a front portion of the lower cantilever leaf spring and a heel wedge positioned under a rear portion of the lower cantilever leaf spring.

15. The prosthetic device of claim 13, wherein the one or more wedges are shaped such that a bottom surface of the one or more wedges is parallel to a ground surface when in use.

16. The prosthetic device of claim 13, wherein the lower cantilever leaf spring comprises a first material, the one or more upper cantilever leaf springs comprise a second material, and wherein the one or more wedges comprise a third material that is different than the first material and the second material.

17. A prosthetic device, comprising:
an ankle component;
a foot component coupled to the ankle component, wherein the foot component has a longitudinal length configured to extend at least partially along a sagittal plane of a user when the prosthetic device is in use, wherein the foot component has a thickness configured to extend at least partially along a transverse plane of the user when the prosthetic device is in use, and wherein the foot component comprises a lower cantilever leaf spring; and
a coupling mechanism positioned between the foot component and the ankle component, wherein the coupling mechanism couples a rotation of the foot component with respect to the sagittal plane to a rotation of the foot component with respect to the transverse plane, wherein the coupling mechanism comprises a first upper cantilever leaf spring and a second upper cantilever leaf spring each having a transverse cross-section defined by a width configured to extend at least partially along a coronal plane of the user when the prosthetic device is in use and a thickness configured to extend at least partially along the transverse plane of the user when the prosthetic device is in use, and wherein each of the first upper cantilever leaf spring and the second upper cantilever leaf spring are configured to be misaligned with the sagittal plane by a rotation angle when the prosthetic device is in use.

18. The prosthetic device of claim 17, wherein the rotation angle is constant along the longitudinal length of the foot component.

19. The prosthetic device of claim 17, wherein the rotation angle varies along the longitudinal length of the foot component.

20. The prosthetic device of claim 17, wherein the prosthetic device further comprises an elastomer material positioned between the lower cantilever leaf spring and the first upper cantilever leaf spring and the second upper cantilever leaf spring.

* * * * *